US00PP23084P3

(12) United States Plant Patent
Dowling

(10) Patent No.: US PP23,084 P3
(45) Date of Patent: Sep. 25, 2012

(54) ***DIANELLA TASMANICA* PLANT NAMED 'NPW2'**

(50) Latin Name: *Dianella tasmanica*
Varietal Denomination: NPW2

(76) Inventor: Phillip Dowling, Mt. Gambier (AU)

( * ) Notice: Subject to any disclaimer, the term of this patent is extended or adjusted under 35 U.S.C. 154(b) by 0 days.

(21) Appl. No.: 12/802,057

(22) Filed: May 28, 2010

(65) Prior Publication Data

US 2011/0055991 P1 Mar. 3, 2011

(30) Foreign Application Priority Data

Sep. 2, 2009 (AU) ..... PBR 2008/316

(51) Int. Cl.
*A01H 5/00* (2006.01)

(52) U.S. Cl. ..... Plt./424

(58) Field of Classification Search ..... Plt./424
See application file for complete search history.

*Primary Examiner* — Kent L Bell

(57) ABSTRACT

'NPW2' is a distinctive variety of *Dianella tasmanica*, which is characterized by its purple leaf color and stability and uniformity of this trait through successive cycles of asexual propagation.

1 Drawing Sheet

Latin name of the genus and species: The Latin name of the novel variety disclosed herein is *Dianella tasmanica*.

Variety denomination: The inventive variety of *Dianella tasmanica* disclosed herein has been given the variety denomination 'NPW2'.

BACKGROUND OF THE INVENTION

The present invention relates to a new and distinct variety of evergreen perennial *Dianella tasmanica*, which has been named 'NPW2'. *Dianella* are a genus of ornamental grass-like plants. In general, *Dianella tasmanica* has flax-like leaves.

An application for plant breeders' rights for 'NPW2' has been lodged with the Australian Plant Breeders Rights Office, and was received on Sep. 2, 2009 (under Application No. 2008/316), a copy of which is attached hereto.

Parentage: The cultivar 'NPW2' was discovered in 2005 in Mt. Gambier, South Australia, Australia, as a naturally occurring spontaneous mutation of *Dianella tasmanica* 'TR20' (U.S. Plant Pat. No. 18,737). The parent is characterized by a green leaf color. Selection criteria for 'NPW2' was a purple leaf color.

Asexual reproduction. The new variety 'NPW2' was first asexually propagated by vegetative division in the state of South Australia, Australia in 2006 and has been asexually propagated since that time by division and micropropagation. The distinctive characteristics of cultivar 'NPW2' have remained stable and true to type through successive cycles of asexual propagation.

SUMMARY OF THE INVENTION

'NPW2' is a distinctive variety of *Dianella tasmanica*, which is characterized by its purple leaf color and stability and uniformity of this trait through successive cycles of asexual propagation.

BRIEF DESCRIPTION OF THE DRAWINGS

FIG. 1 shows a comparison of leaf color between the parent, *Dianella tasmanica* 'TR20', and *Dianella tasmanica* 'NPW2' plants at approximately 15-months of age. The plant was propagated in a greenhouse and was transferred to the field at six months and grown out in full sun for the final nine months.

DETAILED BOTANICAL DESCRIPTION OF THE VARIETY

The following is a detailed botanical description of a new and distinct variety of *Dianella tasmanica* known as 'NPW2' based upon observations of 15-month old plants grown in nursery pots in full sun in open beds in Clarendon, New South Wales, Australia during spring 2009-winter 2009. Plant observations and descriptions were taken in winter 2009.

Those skilled in the art will appreciate that certain characteristics will vary with older or, conversely, with younger plants. 'NPW2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 2007 edition.

'NPW2' is an evergreen perennial *Dianella tasmanica*. 'NPW2' is a semi-erect plant with broad leaf blades, weak leaf arching, and green to purple leaf color depending on the season.

A botanical description of 'NPW2' and comparisons with other varieties of *Dianella tasmanica* are provided below.

Technical Description of the Variety.

Plant characteristics: Growth habit semi-erect, height medium-tall (mean foliar height in a 200 mm pot is 37.6 cm and the width is observed as 25 cm), shoot density sparse to medium, stem internode length very short (measured as 3 mm).

Leaves: Attitude semi-erect, length medium (average measured length of 360 mm), width broad (mean 22.7 mm), arching is weak, variegation absent, glaucosity of upper side medium to strong, upper side color (waxiness removed) corresponds to yellow green (RHS 146A) with a strong blush of purple (RHS 187A) in cooler weather, primary lower side color (waxiness removed) corresponds to yellow green (RHS 146B) with a blush of purple (RHS 187A) in cooler weather, shape ligulate, apex acute, cross section concave, margin with spines present with medium prominence, midrib lower side with spines present with medium prominence. Base attenuate at basal sheath, basal sheath length is short (measured at 135 mm), basal sheath diameter is small (measured at 13 mm), basal sheath color is red purple (RHS 64A). Basal shoot is short, with the longest shoot without leaf formation measured as 80 mm with a width of 11 mm and red purple color corresponding to RHS 60C.

Basal sheath: Anthocyanin coloration (summer) red-purple with a strong intensity.

Basal shoots: Attitude semi-erect, arrangement cluster.

Flowers: 'NPW2' has never been observed to flower since its origination.

Cold and heat tolerance: 'NPW2' has cold and heat tolerance typical of *Dianella tasmanica.*

Drought tolerance: 'NPW2' has drought tolerance typical of *Dianella tasmanica.*

Pest resistance: 'NPW2' has typical resistance to fungal and bacterial pathogens compared to other similar *Dianella tasmanica* cultivars.

Cultural conditions: 'NPW2' can tolerate low nutrient conditions; it does not like continually wet soil conditions, but can tolerate well-draining sandy soils to very heavy clay soils. pH characteristics of the variety are fairly adaptable.

Comparisons with other *Dianella.*

'NPW2' is characterized by a purple leaf blade color as compared with the parent *D. tasmanica* which has a green leaf blade (RHS 143A).

*Dianella* 'TR20' (U.S. Plant Pat. No. 18,737) is the most similar comparator variety to 'NPW2'. In comparison with 'TR20', cultivar 'NPW2' has a leaf with a strong blush of anthocyanin coloration (RHS 187A) in cooler weather (autumn to spring), where this blush is absent in 'TR20'.

'NPW2' can also be compared to the varieties 'DT23' (U.S. Plant Pat. No. 19,253) and 'Little Devil' (unpatented). 'NPW2' has a medium leaf blade whereas 'DT23' has a broad leaf blade. Anthocyanin coloration is absent in the leaf blade of 'Little Devil' whereas it is present and strongly conspicuous in 'NPW2'.

That which is claimed is:

1. A new and distinct variety of *Dianella tasmanica* plant named 'NPW2', substantially as described and illustrated herein.

* * * * *

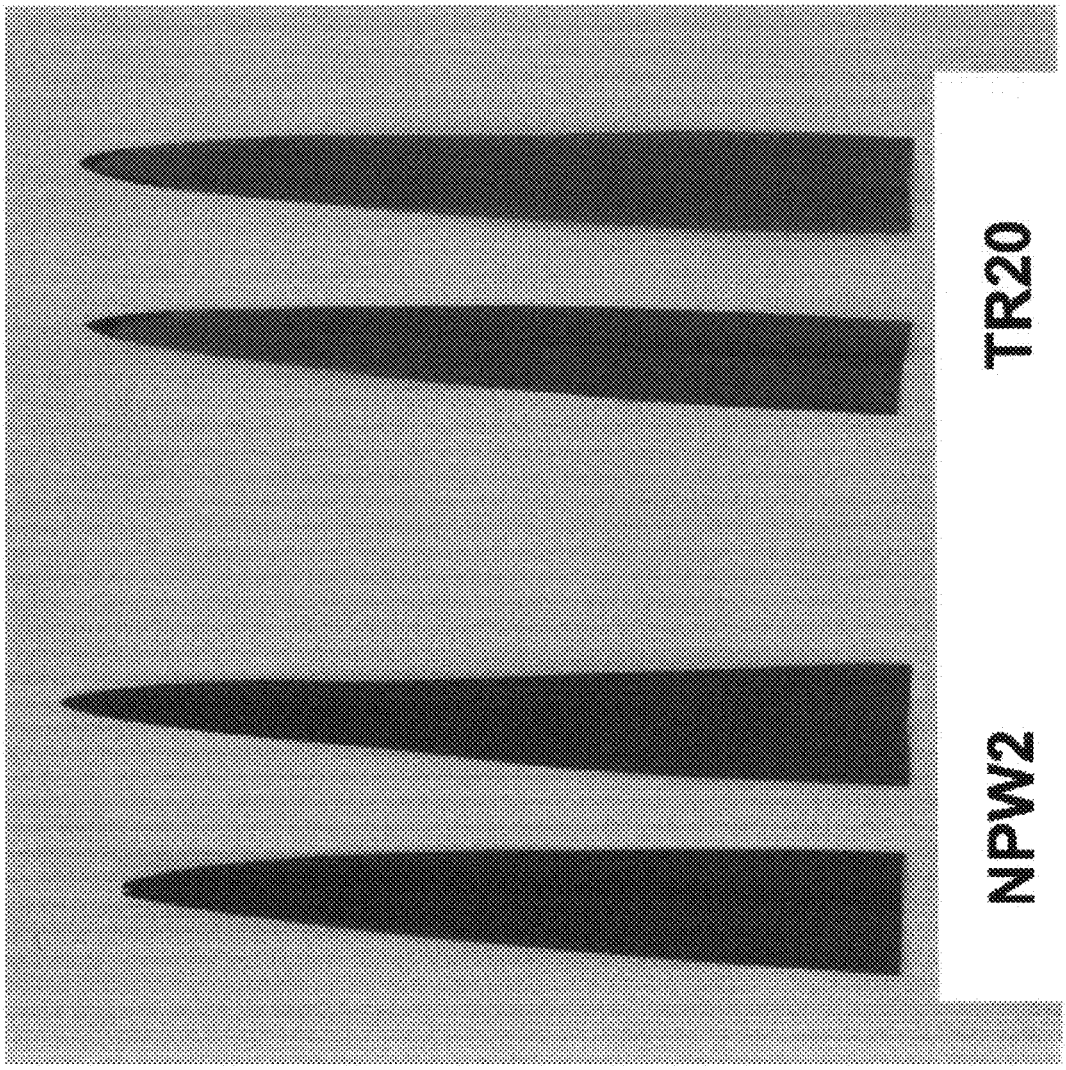
NPW2
TR20